United States Patent [19]

Esko et al.

[11] Patent Number: 5,104,856

[45] Date of Patent: Apr. 14, 1992

[54] HEPARAN SULFATE BIOSYNTHESIS PRIMERS

[75] Inventors: Jeffrey D. Esko; Fulgentius N. Lugemwa, Both of Birmingham, Ala.

[73] Assignee: UAB Research Foundation, Birmingham, Ala.

[21] Appl. No.: 611,255

[22] Filed: Nov. 9, 1990

[51] Int. Cl.$^5$ .................. A61K 31/58; A61K 45/00
[52] U.S. Cl. ............................ 514/26; 514/172
[58] Field of Search ............................ 514/26, 172

[56] References Cited

U.S. PATENT DOCUMENTS 4,882,315 1/1987 Chiodini et al. .................. 514/26

OTHER PUBLICATIONS

Esko et al., *J. Biol. Chem.* (1988) 262:12189–12195.
Lugemwa et al., *Glycoconjugate J.* (1989) 6:457 (Abstract No. 248).
Robinson et al., *Biochem. J.* (1981) 194:575–586.
Robinson et al., *Biochem. J.* (1981) 194:839–846.

*Primary Examiner*—S. J. Friedman
*Attorney, Agent, or Firm*—Morrison & Foerster

[57] ABSTRACT

Conjugates of β-D-xylose with estrogens or modified forms of estrogens are effective in stimulating the synthesis of heparan sulfate, and inhibiting the production of proteoglycan in animal subjects. Accordingly, these conjugates are useful in treating conditions where antithrombotic or antiproliferative activity is desirable.

7 Claims, 3 Drawing Sheets

HEPARAN SULFATE BIOSYNTHESIS PRIMERS

TECHNICAL FIELD

The invention relates to the regulation of glycosaminoglycan (GAG) synthesis. In particular, it relates to a xylose conjugated to estrogen or a modified form thereof which primes heparan sulfate synthesis and inhibits proteoglycan synthesis.

BACKGROUND ART

It is known that animal cells utilize β-D-xylosides to prime glycosaminoglycan (GAG) synthesis. For example, p-nitrophenyl-β-D-xyloside was shown to stimulate the synthesis of chondroitan sulfate in the mutant Chinese hamster ovary cells, pgsA-745 (Esko, J. et al., *J Biol Chem* (1988) 262:12189). In an Abstract recently published by Legumwa, F.N. et al., *Glyconjugate J* (1989) 6:457, it was reported that additional β-D-xyloside conjugates, including those which include 1-octanyl, 1-hexadecanyl, cholesteryl, and farnesyl residues efficiently primed chondroitan sulfate synthesis in these cells. However, the 2-monooleyl glyceryl ether xyloside failed to prime the synthesis of any GAG in this system.

Chondroitan sulfate is only one of a group of GAGs, all of which are biosynthesized through the transfer of xylose units from UDP-xylose to specific serine residues in core proteins to obtain proteoglycans. The transfer of xylose units to the serine residues is followed by transfer of two galactose residues and one glucuronic acid residue to complete the formation of the linkage region tetrasaccharide D-GlcUA-β1,3-D-Gal-β1,3-D-Gal-β1,4-D-Xyl-β1,3-L-[Ser] common to chondroitan sulfate, dermatan sulfate, heparan sulfate and heparin. It appears that at least the first two transferases (xylosyl transferase and galactosyl transferase-I), act on core proteins regardless of their ultimate GAG composition. Synthetic β-D-xylosides, however, appear to stimulate chondroitan sulfate synthesis preferentially.

Galactosyl transferase-I also transfers galactose to synthetic β-D-xylosides to result in the formation of GAG chains (see, for example, Robinson, H.C. et al., *Biochem J* (1981) 194:575–586; Robinson, J.A. et al., *Biochem J* (1981) 194:839–846).

In general, the glycosamino glycans are alternating copolymers of a hexosamine and an alduronic acid which are found in sulfated forms. The members of the GAG family are classified by the nature of the hexosamine/alduronic acid repeating units. In chondroitan sulfates, the alduronic acid is primarily D-glucuronic acid and the hexosamine is acetylated 2-amino-2-deoxy-D-galactose (GalNAc). In heparin and heparan sulfate, the hexosamine is mostly acetylated and sulfated glucosamine (GlcNAc or GlcNS) and the alduronic acid is mostly L-iduronic in heparin and mostly D-glucuronic acid in heparan sulfate. It appears that heparan sulfate is convertible to heparin by conversion of the glucuronic acid residues to L-iduronic acid residues, which conversion involves a change in chirality at the 5C of the uronic acid residue.

Among the GAGs, heparan sulfate and heparin are particularly physiologically important as they are both anticoagulants and also antiproliferative with respect to smooth muscle cells. Thus, elevated levels of these GAGs are helpful in the context of preventing thrombosis and restinosis.

DISCLOSURE OF THE INVENTION

It has been found that unlike prior art conjugates, β-D-xylosides conjugated to estradiol, estrone, and modified forms thereof stimulate the production of heparan sulfate with considerable efficiency. These conjugates thus provide useful pharmaceuticals for prevention of restinosis in patients who have undergone angioplasty and in preventing thrombosis in patients inclined to the formation of blood clots.

Accordingly, in one aspect, the invention is directed to pharmaceutical compositions which contain, as active ingredients, at least one conjugate of β-D-xylose with estradiol, estrone, or conventional modified forms thereof. In other aspects, the invention is directed to methods of treating angioplasty patients and thrombosis-prone patients with the compositions of the invention.

MODES OF CARRYING OUT THE INVENTION

Figure 1:
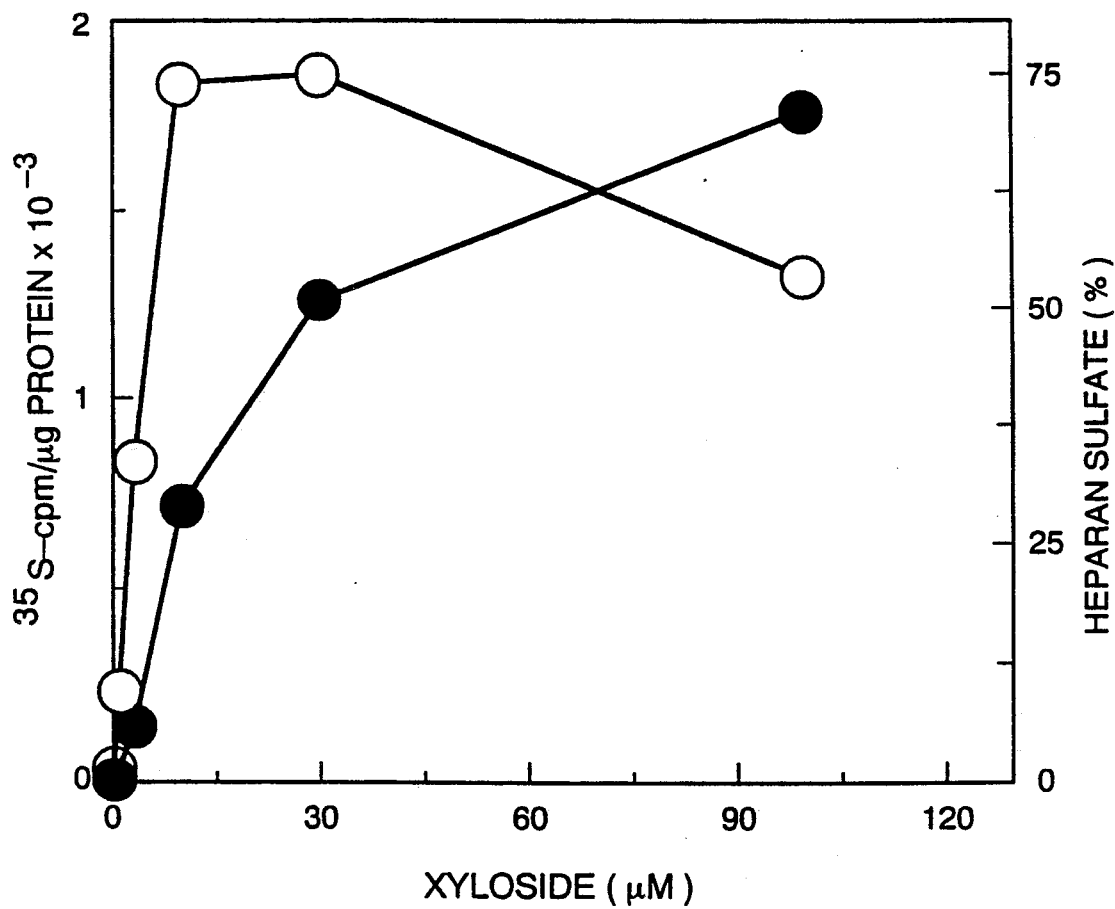
FIG. 1 is a graph showing the dependence of GAG synthesis on estradiol-β-D-xyloside concentration.

The invention is directed to pharmaceutical compositions and methods for their use wherein the active ingredient is at least one conjugate of β-D-xylose with an estrogen or a modified form thereof—specifically, with estradiol, estrone, or the conventional modifications found in manipulation of the steroid hormones. All of the conjugates are through the 1-position of xylose, which is stabilized as the β-anomer in a pyranoside ring. The linkage to the steroid is with the 3-OH in the A ring. Thus, included within the invention is a conjugate of β-D-xylose with estradiol which has the formula:

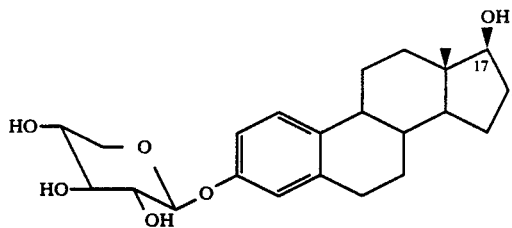

The invention conjugates also include that of β-D-xylose with estrone (wherein, in the above structure, the OH at position 17 is oxidized to a keto group) and those with modified forms of estradiol or estrone, such as the conventional esters (1–6C) at the 17-hydroxyl of estradiol, methylated derivatives at various ring positions, further hydroxylations, and the like. Also included are forms wherein the D-ring is incomplete. General modifications of the steroid hormones, and estrogens in particular, are well known in the art.

SYNTHESIS

The conjugates of the invention are synthesized from acetobromoxylose by the method of Koenigs, W. et al., *Ber* (1901) 34:957–981. In this reaction, estradiol, estrone or other modified forms of the estrogen are conjugated to acetobromoxylose and the products are characterized by spectroscopic methods. Acetobromoxylose is prepared from D-xylose as described by Dale, J.K., *J Am Chem Soc* (1915) 37:2745–2747, and by Barczai-Martos, M. et al., *Nature* (1950) 165:369.

UTILITY AND ADMINISTRATION

The conjugates of the invention stimulate the synthesis of heparan sulfate (they may also inhibit the formation of proteoglycans). Therefore, they are useful in contexts wherein the antiproliferative and/or antithrombosis activity of heparan sulfate is needed.

The compositions of the invention are useful in preventing thrombosis and restinosis in patients with cardiovascular problems. In particular, the compositions of the invention can be administered to patients who have undergone angioplasty to prevent restinosis, in view of the ability of the compositions to stimulate heparan sulfate production, since heparan sulfate inhibits smooth muscle cell proliferation. In addition, the compositions of the invention are useful as antithrombotics and can be administered to patients who are at risk with respect to unwanted blood clot formation.

Administration of the compounds of the invention is generally systemic, typically by injection; however, when properly formulated, oral, transdermal or transmucosal compositions could also be used. For injection, the conjugates are formulated in liquid form, such as in physiological saline, Hank's solution, Ringer's solution and the like, or are prepared in solid forms and taken up in suspension or solution for administration. The administration can be by any suitable route such as intravenous, intramuscular, intraperitoneal, and the like.

For transdermal or transmembrane administration, excipients which effect the transfer of active ingredients across the skin or across mucosal membranes are well known. Excipients include various detergents, including bile salts and fusidates. The transdermal formulations can be applied in the form of skin patches; transmucosal delivery is generally by suppository or through aerosol compositions as is understood in the art.

When properly stabilized, the conjugates of the invention can also be administered orally as tablets, powders, syrups, or capsules.

A wide range of formulations can be used and the choice depends on the selected mode of administration. A suitable practical guide to such formulations is found in *Remington's Pharmaceutical Sciences*, latest edition, Mack Publishing Co., Easton, Pa.

Indications for administration of the compounds of the invention include symptoms or conditions of a subject for whom enhanced levels of heparan sulfate or heparin are desired. In particular, these conditions include cases in which either antithrombotic or antiproliferative activity or both are desired. These conditions include patients at risk for thrombosis formations such as elderly individuals with known cardiovascular problems and individuals at threat for restinosis, such as angioplasty patients. The dosage range for the conjugates of the invention will typically be in the range of 0.01 μg–1 mg/kg per day; however, determination of the correct dosage is generally done by the practitioner and tailored to the individual subject, as is well known in the art. Thus, the dosage employed will depend on the condition of the patient, the manner of formulation, the particular conjugate or mixture thereof chosen, and the judgment of the attending physician.

As noted above, the compositions of the invention may contain as active ingredient only one conjugate of β-D-xylose with the estrogen or modified estrogen or may contain mixtures of such conjugates.

ANTIBODIES

The conjugates of the invention may also be used to raise antibodies in subject mammals, such as mice, rats, sheep, or rabbits, using standard immunization protocols and monitoring of the serum titers. The resulting antisera are useful in immunoassays which can be used to monitor therapy using the conjugates of the invention.

In the immunization protocols, conjugation to carrier may be necessary to confer immunogenicity on the invention conjugates. Formation of such carrier-coupled complexes are well known in the art. Typical carriers include, for example, kehole limpet hemocyanin (KLH) or various serum albumins. Methods to conjugate materials generally to such carriers are known in the art; the hydroxyl groups of the present compounds provide functional groups which permit the employment of, for example, homo- or heterobifunctional linkers such as those marketed by Pierce Chemical Company, Rockford, Ill.

In addition, monoclonal preparations can be obtained by immortalization of the peripheral blood lymphocytes or spleen cells of the immunized animals using methods well known in the art, such as fusion with immortalizing cells as described by Kohler and Millstein.

The following examples are intended to illustrate but not to limit the invention.

EXAMPLE 1

Stimulation of GAG Synthesis by β-D-Xylosides

About $2 \times 10^5$ pgsA-745 cells (which are xylosyl transferase deficient) or pgsB-761 cells (which are galactosyl transferase deficient) or wild-type CHO K1 (CCL-61) cells were seeded into multiple 60 mm diameter dishes in 2 ml Ham's F12 medium. The transferase-deficient cells have been described by Esko, J.D. et al., *Proc Natl Acad Sci USA* (1985) 82:3197–3201; Esko, J.D. et al., *J Biol Chem* (1986) 261:15725–5733; and Esko, J.D. et al., *J Biol Chem* (1987) 262:12189–12195.

After 24 hrs, the medium was replaced with 2 ml sulfate-free medium containing 10 μCi/ml [$^{35}$S]-labeled sulfate and 30 μM of the test β-D-xyloside. After 24 hrs, the labeled GAGs were isolated from the cells and the medium as follows: the medium was removed and the cell monolayers were washed three times with PBS at 4° C. The cells were solubilized with 1 ml 0.1M NaOH and duplicate 50 μl samples were removed for protein determination using BSA as standard. The remainder of the cell extract was adjusted to pH 7 with 10 N acetic acid, combined with spent growth medium and treated with 2 mg/ml of nonspecific protease at 40° C. (Two mg of bovine trachea chondroitan sulfate-A was included as a carrier to insure efficient recovery of GAGs.) After overnight incubation, radiolabeled GAGs were purified by anion exchange chromatography as described by Karen, J.B. et al., *J Biol Chem* (1989) 264:8059–8065.

The amounts obtained were normalized to the amount of cell protein in each dish. As controls, cultures containing no xyloside were labeled in parallel. Portions of the radioactive GAGs were treated with chondroitanase ABC and the resistant material was quantified as heparan sulfate. The chondroitinase ABC digestion was conducted as described by Suzuki, S., *Meth Enzymol* (1972) 28:911-917. The results are shown in Table 1.

TABLE 1

Stimulation of Glycosaminoglycan Synthesis by β-D-xylosides

| Strain | β-xyloside | [$^{35}$S]-labeled GAGs (cpm/μg protein × 10$^{-3}$) | Heparan sulfate (% total) |
|---|---|---|---|
| Wild-type CHO-K1 | None | 400 | 70 |
| Mutant pgsA-745 | None | 4 | ND |
| | Methyl | 1 | 0 |
| | p-Nitrophenyl | 1100 | 6 |
| | n-Octyl | 1200 | 6 |
| | farnesyl | 200 | 0 |
| | Cholesteryl | 100 | 0 |
| | β-Estradiol | 1400 | 45 |
| Mutant pgsB-761 | None | 180 | ND |
| | β-Estradiol | 640 | ND |

As shown in the table, the conjugate with estradiol stood alone in capability to enhance the efficient production of heparan sulfate as opposed to GAGs per se. The p-nitrophenyl-β-D-xyloside and N-octyl-β-D-xyloside stimulated heparan sulfate production only very inefficiently.

EXAMPLE 2

Ability of Estradiol-β-D-Xyloside to Stimulate Heparan Sulfate Synthesis in Mammalian Cells About $2 \times 10^5$ cells of wild-type CHO, BHK, BAE or 3T3 cells were seeded in individual 60 mm diameter culture dishes in 2 ml of DMEM/F12 supplemented with 10% (v/v) fetal bovine serum. After 12 hrs, 1 ml of fresh medium with or without 100 μg cycloheximide was added. Cycloheximide is added to inhibit endogenous proteoglycan synthesis. One hr later, the medium was replaced with 1 ml fresh medium containing 100 μg cycloheximide, 30 μM of estradiol-β-D-xyloside and 100 μCi of labeled sulfate. After 3 hr, the [$^{35}$S]-labeled GAGs were purified and quantitated as described in Example 1, and a portion of the material was treated with chondroitinase ABC to determine the resistant heparan sulfate. The results of this determination are shown in Table 2.

TABLE 2

Estradiol-β-D-xyloside Primes Heparan Sulfate in Various Cell Types

| | No Addition | Cycloheximide | Cycloheximide + Estradiol-β-D-xyloside |
|---|---|---|---|
| | ($^{35}$S-heparan sulfate/μg of cell protein × 10$^{-2}$) | | |
| CHO-K1 | 0.9 | 0.02 | 3.70 |
| BHK | 4.10 | 0.02 | 4.40 |
| BAE | 2.40 | 0.40 | 3.00 |
| 3T3 | 2.00 | 0.02 | 3.00 |

As shown in the table, all cell types showed stimulation of heparan sulfate production in the presence of the conjugate. In CHO-K1 cells, the levels were four times that of normal production.

When the cells were fed xyloside in the absence of cycloheximide, significant stimulation of total GAG synthesis was observed but the amount of labeled heparan sulfate per μg cell protein was the same as in untreated cells.

EXAMPLE 3

Effect of Conjugate Concentration

Approximately $2 \times 10^5$ pgsA-745 cells were plated in 2 ml Ham's F12 medium. After 24 hrs, the medium was changed to 1 ml sulfate-free F12 medium containing 10 μCi of [$^{35}$S]-sulfate and various concentrations of estradiol-β-D-xyloside. The cells were incubated for 3 hrs and the radioactive GAGs were isolated as described in Example 1.

The results are shown in FIG. 1. As shown in the Figure, as the concentration of the xyloside is increased in the range of 5-90 μM, the percentage of heparan sulfate obtained (dark circles) increased consistently. On the other hand, the amount of total GAG synthesized (open circles) began to decline at concentrations higher than about 30 μM. The formation of a significant portion of GAG as heparan sulfate is evident at a concentration of conjugate as low as 10 μM.

EXAMPLE 4

Effect on Growth

Either pgsA-745 or pgsB-761 cells were seeded at a density of $5 \times 10^4$ in 60 mm diameter dishes in the absence or presence of the estradiol-β-D-xyloside conjugate. The cells were harvested at daily intervals with trypsin and quantitated by particle counting. The values obtained were an average of two dishes.

Figure 2A:
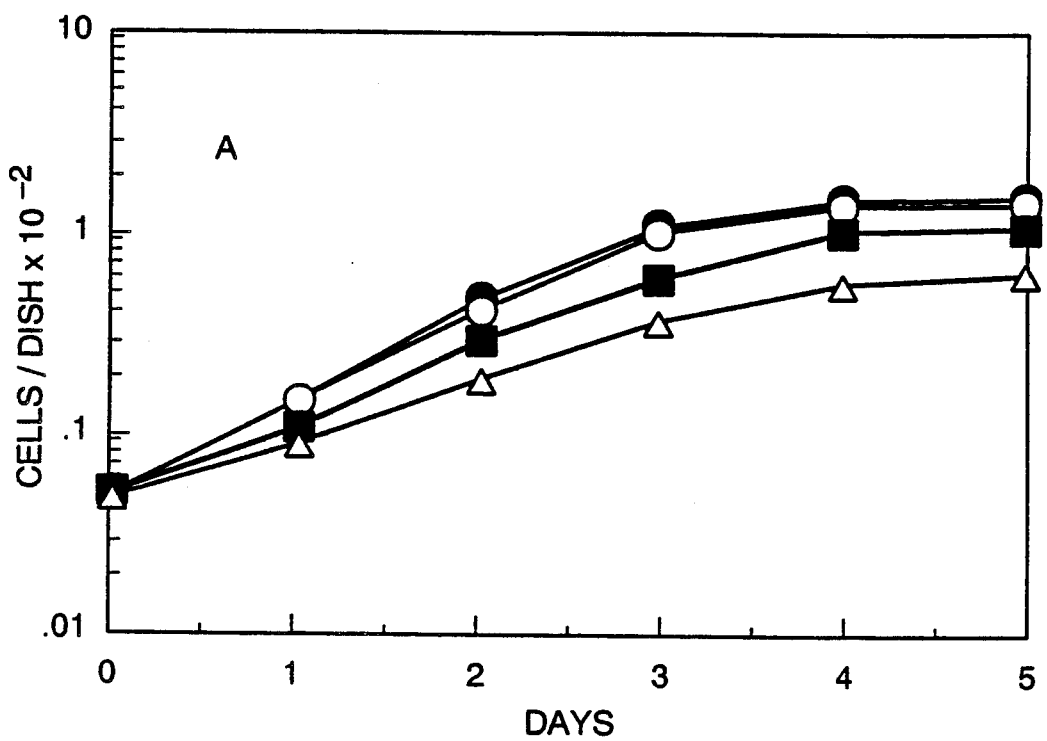
FIG. 2 is a graph showing the effect of estradiol-β-D-xyloside on the growth of mutant CHO cells.
Figure 2B:
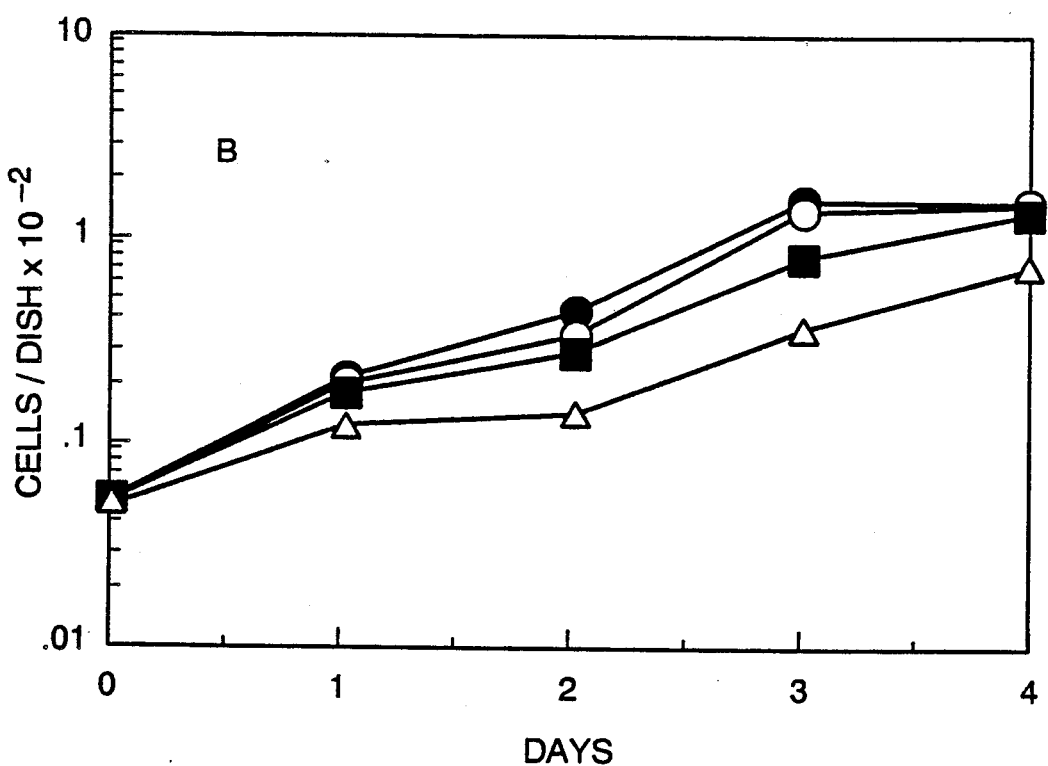

The results are shown in FIG. 2; FIG. 2A represents the results for pgsA-745; FIG. 2B for pGSB-761. In FIG. 2, the dark circles are no additions, open circles 30 μμM, squares 60 μM and triangles 100 μM conjugates.

As shown in FIG. 2A, the addition of 30 μM conjugate did not alter growth, but 60 μM conjugate was partially inhibitory; similar results were obtained as shown in FIG. 2B for pgsB-761 cells, and also for wild-type CHO-K1 cells.

The results shown in FIG. 2 in combination with those of FIG. 1 indicate that the decline in GAG synthesis at high concentrations of conjugate was probably due to inhibition of growth, and because pgsB-761 was similarly affected to pgsA-745, the inhibitory activity was not related to initiation of heparan sulfate chains, but probably is related to the ampiphilic and detergent properties of this compound.

EXAMPLE 5

Characterization of Labeled GAGs and Proteogalactans

Wild-type CHO cells were incubated for 1 hr in 1 ml of F12 medium containing 30 μM estradiol-β-D-xyloside. One mCi of labeled sulfate was added and 30 min later the [$^{35}$S]-labeled proteoglycans were isolated by cooling the radiolabeled cells and medium to 4° C. and adjusting the suspension to 4M guanidine HCl, 0.2% CHAPS, 20 mM N-ethyl maleimide, 2 mM phenylsulfonyl fluoride (PMSF), 0.5 mg/ml leupeptin, 1 mg/ml pepstatin, 10 mM EDTA, and 20 mM xsodium acetate, pH 6.0 (buffer A). The plates were rinsed with 1 ml buffer A and the combined extracts were centrifuged at $20,000 \times g_{av}$ for 30 min. The supernatant was dialyzed twice against 1 L of 4M urea, 0.2% CHAPS, 0.25M NaCl, 20 mM sodium acetate, pH 6.0, containing protease inhibitors (Buffer B). After dialysis, the samples were centrifuged at $10,000 \times g_{av}$ for 30 min to remove a small amount of precipitate. Two mg of bovine trachea chondroitin sulfate A was added as a carrier and the samples were loaded on small columns of DEAE-Sephacel (0.5 ml) equilibrated in buffer B. The columns were washed with 15 ml buffer B and [$^{35}$S]proteoglycans were eluted with 2.5 ml of buffer B adjusted to 1M NaCl. The proteoglycans were desalted by gel filtration chromatography in 10% ethanol (PD-10, Pharmacia-LKB Biotechnology, Inc., Sweden) and lyophilized.

Aliquots of intact proteoglycans were analyzed by gel filtration HPLC and another portion was β-eliminated and the free chains were analyzed. A mixture of proteoglycans and heparan sulfate chains generated in the presence of estradiol-β-D-xyloside was also assayed using the same protocol.

β-elimination to cleave the saccharide from the core protein was achieved incubating [$^{35}$S]proteoglycans with 0.5M NaOH and 1M sodium borohydride at 4° C. for 24 hrs. The reaction was terminated by adjusting the solution to pH 5.5 with acetic acid.

[$^{35}$S]proteoglycans and [$^{35}$S]glycosaminoglycans were desalted on a PD-10 column, lyophilized, resuspended in 20 mM Tris-HCl, pH 7.2, and analyzed by gel filtration HPLC (TSK G4000 SW, 30 cm×7.5 mm inner diameter, LKB Biotechnology). Samples were eluted with 0.5M NaCl in 0.1M KH$_2$PO$_4$, kpH 6.0, containing 0.2% Zwittergent 3-12 (Calbiochem) at a flow rate of 0.5 ml/min in 0.5 fractions. Two and one half ml of Patterson and Green fluid (Patterson, M.S. et al., *Anal Chem* (1965) 37:854–862) was added to each fraction (0.5 ml), and radioactivity was determined by liquid scintillation spectrometry. Blue dextran and disodium salt of ATP were used to determine the $V_o$ and $V_t$ of the column, respectively.

Figure 3:
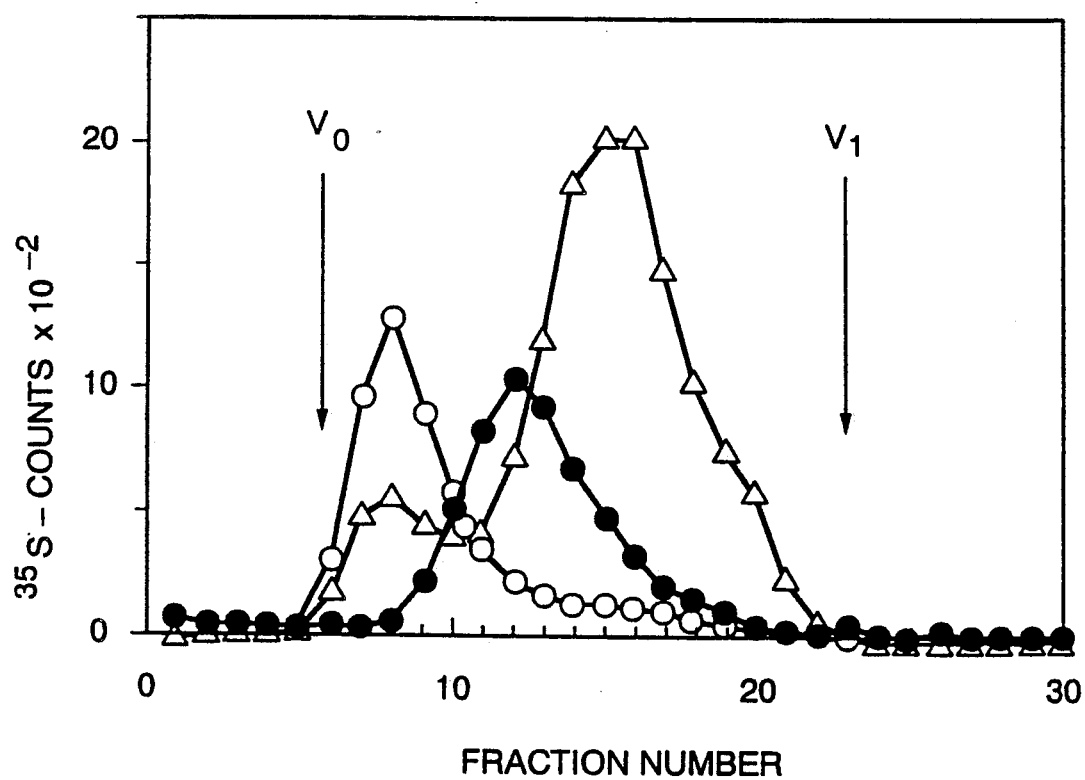
FIG. 3 shows the elution pattern obtained by gel filtration chromatography of labeled proteoglycans and heparan sulfate produced in the presence and absence of estradiol-β-D-xyloside.

These results are shown in FIG. 3 where the triangles indicate the heparan sulfate chains; the dark circles indicate the intact proteoglycan and the closed circles indicate the β-eliminated substrate.

The β-D-xylosides serve as primers because they compete with endogenous xylosylated core proteins for enzymes involved in the remainder of the saccharide chain extension. As shown in FIG. 3, in the absence of estradiol-β-D-xyloside, a major peak of radioactive material eluted at $K_{av}$ of 0.1. When a portion of this material was β-eliminated, the peak disappeared and the released heparan sulfate chains eluted at $K_{av}=0.4$. In the presence of the conjugate, the cells produced less heparan sulfate proteoglycan and accumulated heparan sulfate chains that eluted at $K_{av}$ 0.7. Thus, the conjugate inhibited heparan sulfate proteoglycan biosynthesis. Also, the heparan sulfate chains formed on the xyloside primer were smaller than those formed on the core proteins.

Analysis of the distribution of the conjugate-primed GAG chains showed only 2-10% of the GAGs remained associated with the cells regardless of the type of conjugate.

We claim:

1. A method to prevent or ameliorate thrombosis in animal subjects which method comprises administering to a subject in need of such treatment an effective amount of a conjugate which is a β-D-xyloside coupled through its 1-position to the A-ring hydroxyl of estrone or estradiol or a conventional modification thereof.

2. The method of claim 1 wherein the estrogen is estradiol or estrone.

3. A method to prevent or ameliorate restinosis in an animal subject which method comprises administering to a subject in need of such treatment an effective amount of a conjugate which is a β-D-xyloside coupled through its 1-position to the A-ring hydroxyl of estrone or estradiol or a conventional modification thereof.

4. The method of claim 3 wherein the estrogen is estradiol or estrone.

5. A method to stimulate heparan sulfate production in an animal subject which method comprises administering to a subject in need of such treatment an effective amount of a conjugate which is a β-D-xyloside coupled through its 1-position to the A-ring hydroxyl of estrone or estradiol or a conventional modification thereof.

6. A method to inhibit proteoglycan synthesis in an animal subject which method comprises administering to a subject in need of such treatment an effective amount of a conjugate which is a β-D-xyloside coupled through its 1-position to the A-ring hydroxyl of estrone or estradiol or a conventional modification thereof.

7. A method to inhibit proteoglycan synthesis and/or stimulate heparan sulfate production in cells capable of such synthesis or production which method comprises contacting said cells with an effective amount of a conjugate which is a β-D-xyloside coupled through its 1-position to the A-ring hydroxyl of estrone or estradiol or a conventional modification thereof.

* * * * *